(12) United States Patent
Pereira et al.

(10) Patent No.: US 9,265,441 B2
(45) Date of Patent: Feb. 23, 2016

(54) ASSESSMENT OF TRAUMATIC BRAIN INJURY

(71) Applicants: Francisco Pereira, Princeton, NJ (US); Benjamin Odry, West New York, NJ (US); Hasan Ertan Cetingul, East Windsor, NJ (US)

(72) Inventors: Francisco Pereira, Princeton, NJ (US); Benjamin Odry, West New York, NJ (US); Hasan Ertan Cetingul, East Windsor, NJ (US)

(73) Assignee: SIEMENS AKTIENGESELLSCHAFT, Munich (DE)

(*) Notice: Subject to any disclaimer, the term of this patent is extended or adjusted under 35 U.S.C. 154(b) by 112 days.

(21) Appl. No.: 14/330,814

(22) Filed: Jul. 14, 2014

(65) Prior Publication Data

US 2015/0018664 A1    Jan. 15, 2015

Related U.S. Application Data

(60) Provisional application No. 61/845,427, filed on Jul. 12, 2013.

(51) Int. Cl.
*A61B 5/055* (2006.01)
*A61B 5/00* (2006.01)
*G06F 19/00* (2011.01)
*G06T 7/00* (2006.01)

(52) U.S. Cl.
CPC ............... *A61B 5/055* (2013.01); *A61B 5/0042* (2013.01); *A61B 5/4064* (2013.01); *A61B 5/7267* (2013.01); *G06F 19/345* (2013.01); *G06T 7/0081* (2013.01); *G06T 2207/10088* (2013.01); *G06T 2207/20128* (2013.01); *G06T 2207/30016* (2013.01)

(58) Field of Classification Search
CPC .... A61B 5/0042; A61B 5/055; A61B 5/4064; A61B 5/7267; G06F 19/345; G06T 2207/10088; G06T 2207/20128; G06T 2207/30016; G06T 7/0081
See application file for complete search history.

(56) References Cited

U.S. PATENT DOCUMENTS

2013/0231552 A1    9/2013    Grady et al.

OTHER PUBLICATIONS

C. Chang, et al., "LIBSVM: A Library for Support Vector Machines," Department of Computer Science, National Taiwan University, Taipei, Taiwan, pp. 1-39, 2001/2013.
F. Pereira, et al., "Machine learning classifiers and fMRI: A tutorial overview," NeuroImage 45, pp. S199-S209, 2009.
S. M. Smith, et al., "Advances in functional and structural MR image analysis and implementation as FSL," NeuroImage 23, pp. S208-S219, 2004.
N. Tzourio-Mazoyer, et al., "Automated Anatomical Labeling of Activations in SPM Using a Macroscopic Anatomical Parcellation of the MNI MRI Single-Subject Brain," NeuroImage 15, pp. 273-289, 2002.

*Primary Examiner* — Mark Remaly

(57) ABSTRACT

Traumatic brain injury (TBI) in a patient is assessed. A TBI diagnosis for the patient is determined based on features from MRI data, such as anatomical features, functional features, diffusion features, connectivity features from functional MRI, connectivity features from diffusion MRI, and/or network features from the connectivity features. The TBI diagnosis is determined using a trained classifier. The classifier synthesizes the features into a single number (e.g., a confidence in the prediction of the diagnosis) and indicates the features most responsible for the diagnosis. The disease trajectory for a given patient may be predicted using the trained classifier.

21 Claims, 5 Drawing Sheets influence of ROI-ROI connection
in value of biomarker (% of total )

116 ROIs

116 ROIs contribution map of each ROI towards classifier (% of total)

ASSESSMENT OF TRAUMATIC BRAIN INJURY

RELATED APPLICATIONS

This application claims the benefit of U.S. Provisional Application No. 61/845,427, filed Jul. 12, 2013. The entire contents of the priority document are incorporated herein by reference, except that in the event of any inconsistent disclosure or definition from the present specification, the disclosure or definition herein shall be deemed to prevail.

TECHNICAL FIELD

The present teachings relate generally to brain injuries and, in some embodiments, to the assessment of traumatic brain injury (TBI).

BACKGROUND

Many individuals, by nature of their lifestyles and/or careers, may be at risk for traumatic brain injury (TBI). By way of example, athletes (e.g., especially though not necessarily athletes who participate in high-impact sports, including but not limited to football players, soccer players, boxers, etc.) and soldiers (e.g., especially soldiers exposed to shockwave blasts from explosions) are examples of individuals who may be at higher-than-normal risk for TBI.

Most cases of TBI in sports are deemed "mild" TBI. The examination of suspected injuries tends to be based on psychological tests and, in some instances, structural brain scans. However, for mild TBI, structural brain scans may appear normal, thereby frustrating accurate diagnosis. The decision to return an injured individual to a full range of activity (e.g., returning an athlete to the field of play or returning a soldier to active duty) is oftentimes made based on guidelines that consider the results of psychological tests. Thus, even though a decision may be made that an individual is ready to return to a full range of activity, the individual may still have injury and the recovery process may still be continuing even long after the return to normal activity levels is deemed safe. Returning an individual with TBI to normal activity levels prematurely interferes with the recovery process and places the individual at further risk.

SUMMARY

The scope of the present invention is defined solely by the appended claims, and is not affected to any degree by the statements within this summary.

By way of general introduction, methods are provided for the diagnosis and monitoring of TBI even in situations where the TBI is mild enough that psychological tests or structural brain scans may not detect any brain damage (e.g., sports injuries, battlefield injuries, etc.). In addition, methods are provided for individualized predictions of recovery trajectories for patients based on brain imaging data. As further described herein, methods in accordance with the present teachings leverage information about brain connectivity—both structural and functional—as opposed to only just brain structure. A classifier may use this information for diagnosis and monitoring, as well as for outputting an indication of confidence in the diagnosis or a TBI trajectory for a given patient.

The diagnosis and/or monitoring use structural connectivity (e.g., a matrix that shows the extent to which each pair of brain regions is physically connected that may be derived, for example, from dMRI) and functional connectivity (e.g., a matrix that shows the extent to which resting state activity in one region is correlated with resting state activity in the other). Both of these types of connectivity matrices may be represented as a graph (one node per region), with edges between nodes present if the corresponding regions are connected (and the edge labeled with the strength of the connection). Given such a graph, "network" features of the whole graph may be derived (e.g., the average degree of a node, the average length of a path between nodes, etc.). Using a classifier for deriving network features may provide better diagnosis and monitoring. The confidence output by the classifier may be treated as a synthetic biomarker that explains the decision for that particular patient in terms of the various types of features collected. The synthetic biomarker values may, if obtained for each subject at the beginning and end of a period, be used together with the imaging data to learn a regression model capable of predicting the evolution of disease trajectory over that period.

A computer-implemented method for assessing a traumatic brain injury (TBI) in a patient in accordance with the present teachings includes: obtaining diffusion magnetic resonance imaging (dMRI) data from the patient; obtaining resting-state functional magnetic resonance imaging (rs-fMRI) data from the patient; extracting connectivity features between different regions of a brain of the patient from the rs-fMRI data obtained from the patient and/or from the diffusion magnetic resonance imaging (dMRI) data obtained from the patient; extracting network features from the connectivity features; and determining a TBI diagnosis for the patient based on at least the network features and the connectivity features using a trained classifier A first system for assessing a traumatic brain injury (TBI) in a patient in accordance with the present teachings includes: a computer processor; a non-transitory memory coupled with the computer processor; first logic stored in the non-transitory memory and executable by the computer processor to cause the computer processor to extract features from magnetic resonance imaging (MRI) data obtained from the patient; second logic stored in the non-transitory memory and executable by the computer processor to cause the computer processor to determine a TBI diagnosis for the patient based on the features using a trained classifier; third logic stored in the non-transitory memory and executable by the computer processor to cause the computer processor to output a confidence in the TBI diagnosis as a synthetic biomarker; fourth logic stored in the non-transitory memory and executable by the computer processor to cause the computer processor to output a measure of feature influence indicative of a relative influence of a feature on the TBI diagnosis for the patient; and fifth logic stored in the non-transitory memory and executable by the computer processor to cause the computer processor to output a prediction of a recovery trajectory for the patient based on the features using the trained classifier.

A second system for assessing a traumatic brain injury (TBI) in a patient in accordance with the present teachings includes: means for extracting anatomical features from structural magnetic resonance imaging (sMRI) data obtained from the patient; means for extracting functional features from resting-state functional magnetic resonance imaging (rs-fMRI) data obtained from the patient; means for extracting connectivity features from the rs-fMRI data obtained from the patient and/or from diffusion magnetic resonance imaging (dMRI) data obtained from the patient; and means for determining a TBI diagnosis for the patient based on at least the anatomical features, the functional features, and the connectivity features using a trained classifier.

A non-transitory computer readable storage medium in accordance with the present teachings has stored therein data representing instructions executable by a programmed processor for assessing a traumatic brain injury (TBI) in a patient. The storage medium includes instructions for: (a) extracting anatomical features from structural magnetic resonance imaging (sMRI) data obtained from the patient; (b) extracting functional features from resting-state functional magnetic resonance imaging (rs-fMRI) data obtained from the patient; (c) extracting connectivity features from the rs-fMRI data obtained from the patient and/or from diffusion magnetic resonance imaging (dMRI) data obtained from the patient; and (d) determining a TBI diagnosis for the patient based on at least the anatomical features, the functional features, and the connectivity features using a trained classifier.

DETAILED DESCRIPTION

An approach for assessing a traumatic brain injury (TBI) in a patient has been discovered and is described herein. The approach may be used to provide one or more of (a) a diagnostic of whether a new subject has TBI based on imaging data obtained from the subject, (b) an indication of confidence in the prediction, and/or (c) an explanation of what damage contributed to the prediction. In addition, the approach may be used to provide a personalized recovery trajectory based on brain imaging data and other patient-specific factors (e.g., genetic information, phenotypic information, test results, etc.). As further described herein, methods in accordance with the present teachings may use imaging data from an existing dataset to train a diagnostic classification model that distinguishes patients from controls and that explains the decision whereby the patients are distinguished from the controls. A regression model may be trained to make an individualized prediction of recovery that relies on the output of the classification model at the beginning and end of a collection period, as well as the imaging data collected for the subject.

It is to be understood that elements and features of the various representative embodiments described below may be combined in different ways to produce new embodiments that likewise fall within the scope of the present teachings.

Figure 1:
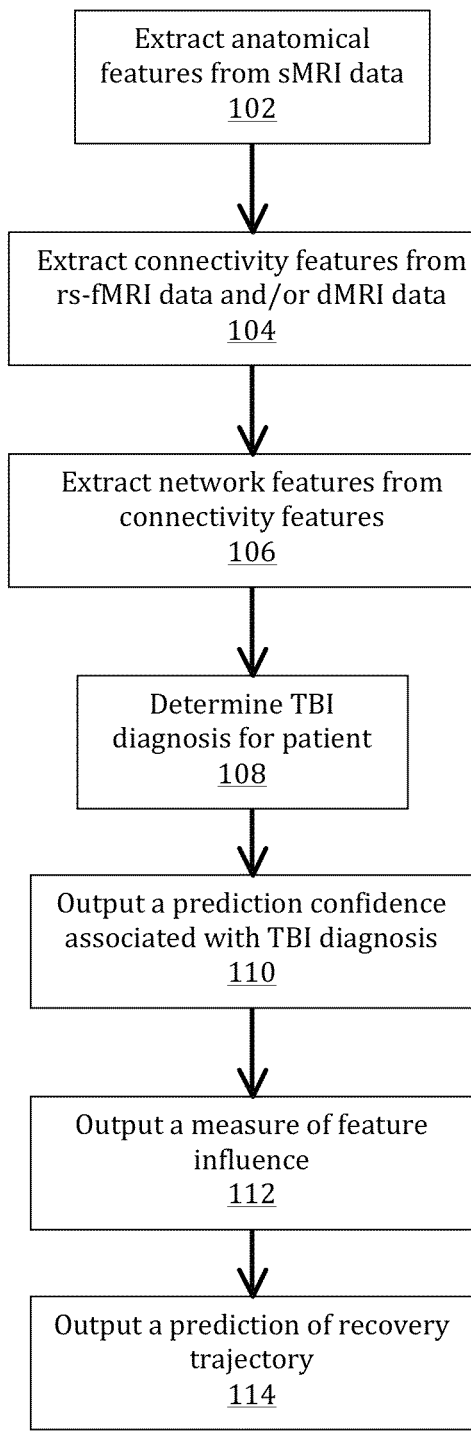
FIG. 1 shows a flow chart of an exemplary process 100 for assessing a traumatic brain injury (TBI) in a patient in accordance with the present teachings.

By way of general introduction, as shown in FIG. 1, an exemplary method 100 for assessing a traumatic brain injury (TBI) in a patient in accordance with the present teachings includes: (a) extracting 102 anatomical features from structural magnetic resonance imaging (sMRI) data obtained from the patient; (b) extracting 104 connectivity features from resting-state functional magnetic resonance imaging (rs-fMRI) data and/or from diffusion MRI (dMRI) data obtained from the patient; (c) extracting 106 network features derived from the connectivity features; and (d) determining 108 a TBI diagnosis for the patient based on at least the network features and the connectivity features using a trained classifier. Other patient characteristics from any source may be used by the trained classifier for the diagnosis. A confidence score in the diagnosis may be output by the trained classifier.

As used herein, the term "assessment" as used in reference to TBI refers broadly to an evaluation, estimation, and/or prediction relating to one or a plurality of aspects of TBI. Representative types of assessments include but are not limited to diagnosis, prediction of recovery trajectory, ranking of a measure of feature influence, identification of a feature influence, and the like, and combinations thereof.

In some embodiments, as shown in FIG. 1, a method for assessing a traumatic brain injury (TBI) in a patient in accordance with the present teachings further includes one or more of the following additional acts: (e) outputting 110 a prediction confidence associated with the TBI diagnosis for the patient; (f) outputting 112 a measure of feature influence indicative of a relative influence of a feature on the TBI diagnosis for the patient; and/or (g) outputting 114 a prediction of a recovery trajectory for the patient based on at least the network features and the connectivity features using the trained classifier.

It is to be understood that the relative ordering of some acts shown in the flow chart of FIG. 1 is meant to be merely representative rather than limiting, and that alternative sequences may be followed. Moreover, it is likewise to be understood that additional, different, or fewer acts may be provided. By way of non-limiting and representative example, in FIG. 1, the act of outputting 110 a prediction confidence is shown as preceding the act of outputting 112 a measure of feature influence. However, in alternative embodiments, the sequence of act 110 and act 112 may be reversed. In addition, one or more of the acts depicted in FIG. 1 may occur substantially contemporaneously and/or in a different sequential order than the representative sequences shown in FIG. 1.

In some embodiments, a method for assessing a traumatic brain injury (TBI) in a patient in accordance with the present teachings is implemented using a computer and, in some embodiments, one or a plurality of the acts of (a) extracting 102; (b) extracting 104; (c) extracting 106; (d) determining 108; (e) outputting 110; (f) outputting 112; and/or (g) outputting 114 described above are performed by one or a plurality of processors.

In some embodiments, as described above, the present teachings provide methods for assessing a traumatic brain injury (TBI) in a patient. In other embodiments, as further described below, the present teachings also provide systems for assessing a traumatic brain injury (TBI) in a patient.

Figure 2:
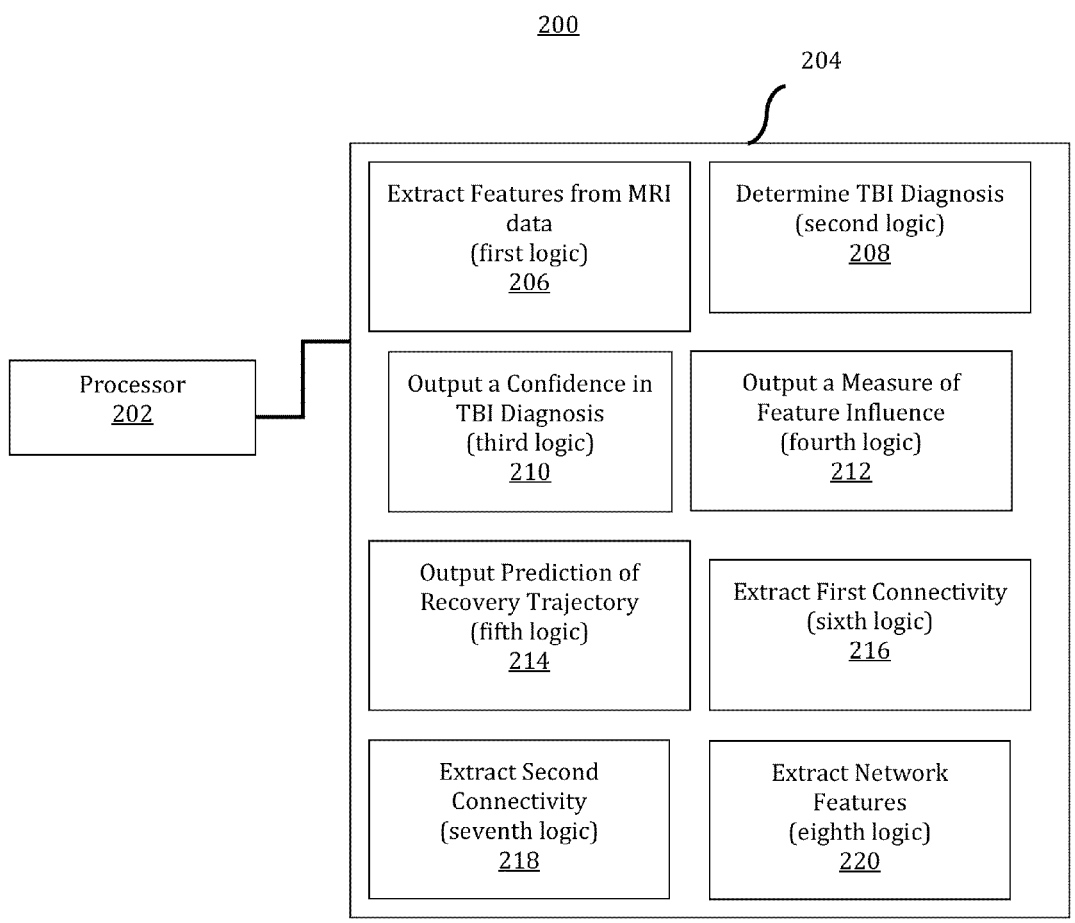
FIG. 2 shows a block diagram of an exemplary system 200 for assessing a traumatic brain injury (TBI) in a patient in accordance with the present teachings.

By way of example, FIG. 2 shows a block diagram of a representative first system 200 for assessing a traumatic brain injury (TBI) in a patient in accordance with the present teachings. In some embodiments, as shown in FIG. 2, a system 200 for assessing a traumatic brain injury (TBI) in a patient in accordance with the present teachings is implemented as part of a diagnosis module and/or a prediction module in a computer system. As shown in FIG. 2, the system 200 includes: a computer processor 202; a non-transitory memory 204 coupled with the computer processor 202; first logic 206 stored in the non-transitory memory 204 and executable by the computer processor 202 to cause the computer processor 202 to extract features from magnetic resonance imaging (MRI) data obtained from the patient; second logic 208 stored in the non-transitory memory 204 and executable by the computer processor 202 to cause the computer processor 202 to determine a TBI diagnosis for the patient based on the features using a trained classifier; third logic 210 stored in the non-transitory memory 204 and executable by the computer processor 202 to cause the computer processor 202 to output a confidence in the TBI diagnosis as a synthetic biomarker; fourth logic 212 stored in the non-transitory memory 204 and executable by the computer processor 202 to cause the computer processor 202 to output a measure of feature influence indicative of a relative influence of a feature on the TBI diagnosis for the patient; and fifth logic 214 stored in the non-transitory memory 204 and executable by the computer processor 202 to cause the computer processor 202 to output a prediction of a recovery trajectory for the patient based on the features using the trained classifier. Other logic may be provided for extracting network features from the connectivity features.

By way of example, in some embodiments, the apparatus 200 may further include one or more of the following: sixth logic 216 stored in the non-transitory memory 204 and executable by the computer processor 202 to cause the computer processor 202 to extract a first connectivity of different regions of the patient using functional MRI; seventh logic 218 stored in the non-transitory memory 204 and executable by the computer processor 202 to cause the computer processor 202 to extract a second connectivity of the different regions of the patient using diffusion MRI; and/or eight logic 220 stored in the non-transitory memory 204 and executable by the computer processor 202 to extract network features for the first connectivity and/or the second connectivity.

In some embodiments, the system 200 may be coupled to other modules of a computer system and/or to databases so as to have access to relevant information as needed (e.g., patient medical history, an MRI scanning device, etc.) and initiate appropriate actions.

One or more modules or logic described herein may be implemented using, among other things, a tangible non-transitory computer-readable medium comprising computer-executable instructions (e.g., executable software code). Alternatively, modules may be implemented as software code, firmware code, hardware, and/or a combination of the aforementioned. For example, the modules may be embodied as part of an image acquisition device, such as an MRI scanning device.

In some embodiments, the present teachings relate to a method and system for diagnosis of traumatic brain injury (TBI) from magnetic resonance images. A digital image may be composed of digital representations of one or more objects (or shapes). The digital representation of an object may be described herein in terms of identifying and manipulating the objects. Such manipulations are virtual manipulations accomplished in the memory or other circuitry/hardware of a computer system. Accordingly, some embodiments may be performed within a computer system using data stored within the computer system.

FIG. 1 illustrates representative acts in an exemplary method 100 for diagnosis of TBI in accordance with the present teachings. The method of FIG. 1 may transform medical image data representing a patient's brain to extract a large number of features from the medical image data, and may determine a diagnosis of the patient based on the extracted features using machine-learning techniques. In some embodiments, a structural MRI, a functional MRI series, a diffusion MRI series, and phenotypic data of a patient are received. The structural MRI is an image showing anatomical details of the patient's brain acquired using an MRI scanning device, and may be acquired using a particular contrast sequence (e.g., T1). The structural MRI may be provided in a standard digital format, such as NIFTI-1. The structural MRI may be received directly from an MRI scanning device or may be received by loading a previously stored structural MRI of the patient. The functional MRI series is acquired from an MRI scanning device while the patient is at rest in the device (e.g., "resting state" or rs-fMRI). The functional MRI series is acquired with a particular contrast sequence (e.g., T2) and may also be provided in a standard digital format. The functional MRI series is referred to herein as rs-fMRI for resting-state fMRI. The diffusion MRI (dMRI) series is acquired from an MRI scanning device configured to sense molecular diffusion in the patient.

At act 102 of FIG. 1, anatomical features are extracted from the structural MRI. Any set of anatomical features may be extracted. Below are some example features. Once the structural MRI volume of the patient is read into random access memory of a computer system, the grey matter and white matter are segmented in the structural MRI. The structural MRI volume may be processed based on the stored image intensity values of its voxels and neighborhood relationships to determine which voxels are white matter and which voxels are grey matter. The grey matter and white matter segmentation may be performed using any brain segmentation method including but not limited to FMRIB's Automated Segmentation Tool (FAST). Based on the segmentation results, a boundary is detected between the grey matter and white matter in the structural MRI. A 3D-reconstruction of the patient's cortical surface is generated based on the detected boundary. In addition to segmenting the patient's cortical structures, individual subcortical brain structures are also segmented. Each of the two cortical hemisphere surfaces is registered to a pre-computed spherical brain atlas by finding an optimal alignment of the cortical folding patterns. Techniques for reconstructing the cortical structures, segmenting the subcortical brain structures, and registering the cortical surfaces to a predetermined atlas are available and may be included in various image processing software packages such as FSL, AFNI or SPM.

At each of a set of uniformly-spaced locations in each cortical hemisphere corresponding to sample locations of an icosahedron model defined in the spherical brain atlas coordinate space, the following two scalar-values quantities are calculated: cortical thickness and mean curvature. Cortical thickness is calculated as the distance from the boundary between the gray and white matter to the pial surface boundary measured normal to the local surface tangent. Mean curvature is calculated as the average curvature of the local cortical surface, measured as an average of two principal curvatures and smoothed spatially. These quantities are written to the patient's feature list, which is stored on an electronic storage device.

Another anatomical feature calculated is surface area of individual cortical parcels. Cortical parcels are spatially contiguous portions of a full cortical hemisphere. Each vertex in the patient's cortical hemisphere may belong to only one parcel, and its parcel membership is estimated using a Bayesian method that incorporates local curvature information and a set of spatial prior probabilities that represent the likelihood that each vertex in the atlas coordinate space belongs to each parcel. Once each vertex of a cortical hemisphere is assigned to a parcel, the surface area of each parcel is estimated, and these values are stored in the patient's feature list. In addition to surface area, other statistics (e.g., average cortical thickness, volume, mean curvature, and standard deviations for each measure) may be calculated for each cortical parcel.

Similarly, volume-based subcortical segmentation is used to segment the subcortical brain structures, and the volumes of the subcortical brain structures are calculated and normalized by the patient's intracranial volume to help control for age effects, and then stored in the patient's feature list. Volumes of subcortical areas with hypointensities in gray or white matter are also calculated and normalized by the patient's intracranial volume, and then stored in the patient's feature list.

In some embodiments, methods in accordance with the present teachings further include extracting functional features from the rs-fMRI data. The data may be used by the trained classifier. Any functional features may be extracted. Below are some examples. In some embodiments, the functional features are extracted by generating a network representing functional connectivity between various regions in the brain and then extracting network features from the network. In some embodiments, a respective rs-fMRI time series is extracted for each of a plurality of brain regions. The rs-fMRI data for a patient contains multiple image volumes (e.g., a volume time series) acquired one after the next in an MRI scanning device. The rs-fMRI data and the structural MRI for the patient are processed as follows to extract a respective time series for each of a plurality of brain regions. The patient's structural MRI image is warped into a "template space" defined by a standardized image template, such as the MNI 152. The warping is achieved by calculating a globally optimal affine transformation that minimizes difference between the patient's structural MRI and the template image. A low-dimensional nonlinear deformation that further optimizes the match to the template may be solved. The calculated affine transformation and nonlinear deformation may be stored in a digital storage device for later use.

The volumes containing the initial 10 seconds of the patient's rs-fMRI data may be discarded. Temporal interpolation may then be performed on each image volume in the rs-fMRI data to correct for differences in the time at which each portion of the image volume was acquired. The interpolated images may be stored in a digital storage device in a standard format for further processing. Once the interpolation is performed on each image volume in the rs-fMRI data, each image volume is aligned to the first remaining image volume in the series by computing optimal parameters of a rigid body (e.g., 6-parameter affine) transformation.

All rs-fMRI data estimated to not originate from within the brain is then discarded from each of the rs-fMRI image volumes. Intensity-based and neighborhood-based segmentation techniques may be used to estimate which voxels each rs-fMRI image volume belongs to (e.g., gray matter, white matter, and cerebrospinal fluid). All other voxels may be discarded from the rs-fMRI images.

An affine image transformation (e.g., with seven degrees of freedom) is calculated to optimally co-register the rs-fMRI data with the structural MRI data. The registered rs-fMRI data is transformed in the "template space" by applying the transformations calculated to warp the structural MRI image volume to the "template space." The transformed rs-fMRI data are then resampled to a three-dimensional grid in the template space, thereby resulting in a time series for each voxel of the resampled rs-fMRI data in the template space.

Linear regression over the time series for each voxel is used to remove effects in the rs-fMRI that are correlated with the mean time course of the measured signal calculated in voxels estimated to be from white matter and cerebrospinal fluid. That is, for each voxel, the average intensity over the time series from the white matter and cerebrospinal fluid is calculated and regressed out to estimate the intensity caused by the gray matter for that voxel in order to extract the rs-fMRI data that is driven by activity of the cortex. A bandpass filter is applied to isolate portions of the rs-fMRI that are within a predetermined frequency range. In an exemplary implementation, a bandpass filter isolates portions of the rs-fMRI that are within the bands $0.009 < f < 0.08$ Hz. This bandpass filtering removes signals (voxel time series) with very low frequency corresponding to long term changes at a particular voxel and removes signals having very fast fluctuations, which are likely noise. The resulting rs-fMRI may be convolved with a 3D-Gaussian smoothing kernel to provide spatial smoothing of the rs-fMRI data. In an exemplary implementation, a 3D Gaussian kernel with width of 6 mm at full-width, half maximum may be used to provide the spatial smoothing. The resulting rs-fMRI data is stored in an electronic/digital storage device.

The total dataset of the rs-fMRI data may be reduced by averaging the rs-fMRI time courses within anatomical regions of interest (ROIs). The ROIs are defined by a digital brain atlas that is defined in the template space and uniquely maps which voxels in the rs-fMRI data (transformed to the template space) belong to each of M distinct brain regions. For each brain region, the system extracts a single vector time series representing the rs-fMRI activity of that brain region. This results in a matrix of size M×N, where N is a number of rs-fMRI volumes used to generate the time series (e.g., a number of volumes acquired minus four). The M×N matrix containing the time series for each ROI may be stored to an electronic storage device for later processing.

In some embodiments, the Automated Anatomical Labeling (AAL) atlas, which defines 116 brain regions, may be used as the brain atlas. In an alternate implementation, the atlas is refined further before extracting each single vector time series by first removing from each ROI voxels likely to be located in white matter for the patient, as determined from the segmentation of the structural MRI, and then subdividing each ROI into sub-ROIs by identifying groups of voxels in the ROI with similar time series and assigning them to the same sub-ROI.

A network graph representing functional connectivity between the brain regions may be generated based on the rs-fMRI time series for each brain region. According to an advantageous embodiment, an M×M affinity matrix that shows a connectivity or relatedness between the M brain regions is constructed from the M×N matrix of brain region time series. The affinity matrix is then converted to a binary matrix in which only values above a certain threshold (representing significant correlations between brain regions) are kept, and a network graph is generated from the binary affinity matrix. The network graph includes M nodes representing the M brain regions and edges connecting nodes having significant correlations, and the edge weights are determined by the values in the binary affinity matrix.

In one possible implementation for generating the network graph, the network graph may be calculated using a Sparse regularized Inverse Covariance (SIC) matrix. In this implementation, a correlation matrix is first calculated from the M×N matrix of brain region time series, resulting in an M×M correlation matrix. The correlation matrix may be calculated by calculating a covariance between the respective time series extracted for each possible pair of brain structures. The inverse of this matrix is then iteratively calculated using a numerical method that regularizes the solution by minimizing the L1-norm to promote a sparse solution. This process involves a free parameter, the regularization parameter λ, for which different values will result in different networks. In an exemplary implementation, matrix inverses may be calculated using multiple values of λ, within a certain range (e.g., from 0.25 to 0.60), and for each inverse matrix, the average sum of each column of the matrix is calculated. The solution for which this value is minimal is then preserved and that solution is stored in a storage device. Other solutions are discarded. Entries along the diagonal of the inverse correlation matrix are set to zero, all entries with a value less than a threshold parameter are also set to zero, and the resulting binary inverse correlation matrix is stored in an electronic storage device for further processing. An alternative implementation may consider a wider range of λ, values and use split-half cross-validation to determine the optimum value of the parameter. In another alternative implementation a predetermined λ, value (e.g., 0.1) may be used in all cases.

The M×M inverse correlation matrix is then cast as the weighted adjacency matrix of a network graph including M nodes with edges connecting related nodes. For example, in the case in which there are 116 brain regions, the network graph includes 116 nodes and a possible 6,670 undirected edges (not allowing connections from a node to itself). Each edge from node i to node j is assigned a weight, which is the value in the inverse correlation matrix at entry (i,j). These real values edge weights may be interpreted as "distance weights" or "affinity weights" as appropriate to the network measures being computed, as described below.

In another possible implementation for generating the network graph, a weighted adjacency matrix may be generated from the M×N matrix of brain region time series by calculating the Pearson correlation coefficients between the average time series for all pairs of brain regions. The Pearson correlation coefficients are then converted to P-values under the null hypothesis of no correlation, using a Fisher transformation and taking into account temporal autocorrelation of the rs-fMRI signal to determine the effective number of degrees of freedom. A false-discovery rate may be used to correct for multiple comparisons at a rate of 0.01. Edges representing significant correlation between nodes are assigned weights equal to the corresponding correlation coefficients in the matrix, and edges for which the corrected correlations were not significant are set to zero.

In some embodiments, network features are extracted from the network graph. The network graph may be expressed as $G=\{V,E\}$ including a set of vertices (or nodes) V, and edges E. An individual $i^{th}$ vertex is denoted as $v_i \epsilon V$ and an edge spanning vertices $v_i$ and $v_j$ is denoted as $e_{ij} \epsilon E$. The weight assigned to edge $e_{ij}$ is denoted as $w_{ij}$. In some embodiments, inferred edges between the nodes representing the brain regions are weighted using real-values representing a correspondence between the nodes. That is, although the matrix used to determine which nodes are connected by weighted edges is referred to above as a "binary matrix," the edge weights are not binarized. The absolute values of the edge weights are used to calculate the network features. The edge weights computed in the network construction methods described above are affinity weights, which are larger if two nodes are more strongly connected. Accordingly, in order to calculate meaningful network features based on paths, the edge weights may be converted to distance weights, which are small if nodes are similar. The relationship between affinity weights and distance weights is expressed as: $w_{distance}=[1/(w_{affinity})]$. A number of network features may be extracted from the network graph generated for the patient, as described below.

For each of the M nodes, the weighted node degree may be calculated as the sum of the weights of all edges connected to that node. The M node degree values are then appended to the list of features for the patient.

For each of the M nodes, a betweenness value may be calculated. The betweenness for a node i defined as the fraction of optimal paths between every pair of nodes in the network that pass through the node i. An optimal path is defined as a path with the minimum sum of edge weights along the path. The M betweenness values are then appended to the patient's list of features.

2-Cliques are the edge weights between pairs of nodes in the network graph. The values of all 2-cliques (e.g., the edge weights between each pair of nodes in the network graph) are stored in the patient's feature list.

For each of the M nodes, an eccentricity value is calculated. The eccentricity value for a node is calculated by determining the shortest path from that node to each other node (e.g., the path with the minimum sum of edge weights), and then finding the maximum of these shortest paths to any other node in the network graph. The M eccentricity values (one per node) are stored in the patient's feature list.

The rs-fMRI network graph may be cast as a linear resistive circuit, in which the edge weights server as resistances. In particular, the Moor-Penrose pseudo-inverse of the graph Laplacian of the rs-fMRI network is calculated. After removing diagonal entries in the Laplacian matrix, the maximum value in each column is computed, which defines the pseudo-eccentricity measure on a per-node basis. These M pseudo-eccentricity values are stored in the patient's feature list.

The rs-fMRI adjacency matrix may be used as the information matrix in a Gaussian Markov Random Field model of rs-fMRI activity. In particular, the rs-fMRI time series are considered as couple Gaussian random variables and the probability of observing each of the multivariate activity states (across M brain regions) observed in the patient's data. It is determined which of the observed states is most probable as the activity at each of the M nodes at each time point, and the most probable activity state for each node at each time point is stored in the patient's feature list.

In some embodiments, the B0 image from dMRI data may be registered to the reference structural image using "flirt" with 6 DOF. The inverse transformation may be applied to the subject-specific atlas to register the subject-specific atlas to the dMRI data. Diffusion may be represented with any parametric or non-parametric diffusion model (e.g., diffusion tensors, orientation distribution functions, higher-order tensors, etc.), which is estimated from the dMRI data. The white matter circuitry is inferred via whole-brain tractography (e.g., based on deterministic, probabilistic, or global formulations), which delineates fiber pathways until some user-specified termination criteria are met (e.g., low fractional anisotropy, limited track curvature).

In some embodiments, brain connectivity information may be obtained from imaging data as described below. For example, both rs-fMRI and dMRI may be used to produce connectivity matrices (e.g., matrices that quantify the extent to which pairs of brain regions of interest are connected for that type of data). The data for each subject includes dMRI data and sMRI data. Structural connectivity matrices may be produced as follows. Given a fiber track physically connecting ROIs i and j, different scalar measures computed from the underlying diffusion models along the track may be used to quantify the connectivity between the regions. For example, fractional anisotropy (FA), mean diffusivity (MD), and axial/radial1/radial2 diffusivities (AD/RD1/RD2) may be used. For each measure, the connectivity of the track may be defined to be the mean value of the measure along the track, and all ROIs with a track segment between them deemed to be connected. For each measure used, this process may yield a 116×116 matrix, with entry (i, j) containing the connectivity value between ROIs i and j, as shown, for example, in FIG. 3A.

The present teachings are not limited to the above-described network features, and other types of network features may be extracted using the patient's network graph as well. For example, features representing additional measures of graph connectivity (e.g., average path length, diameter, radius, and mean/max/min clustering coefficients), features representing network separability, features characterizing the cyclic structure of the network, and/or features representing sparsity measurements of the network may also be calculated in addition to the above described network features.

Using structural, functional, or diffusion MRI data, any number of connectivity and/or network features may be calculated. In some embodiments, structural features, functional and diffusion connectivity features, and corresponding network features are extracted.

Returning to FIG. 1, at act 108, a TBI diagnosis for the patient is determined based on the features, and—in some embodiments—phenotypic features of the patient using a trained classifier. In particular, the patient's feature list, including the anatomical features, the functional and diffusion connectivity features, the network features, and the phenotypic features, is read from an electronic storage device, a pre-determined set of those features (determined during training) are selected, and the patient-specific values for the selected features are arithmetically combined by a trained classification module to determine a diagnosis of TBI-positive or TBI-negative for the patient. The diagnosis is output, for example, by displaying the diagnosis on a display device of a computer system, and the diagnosis is saved to a storage device. Furthermore, a numeric degree of confidence may be produced by the trained classification module, as shown at act 110. In addition, a report of which features had an impact in the diagnosis may be produced, as shown at act 112.

Representative phenotypic features of a patient may include but are not limited to the patient's age, gender, handedness (e.g., left- or right-handed), verbal 10, and performance 10. The age of the patient may be represented in a floating-point format, including fractions of years. The gender of the patient may be represented by a binary value: for example, 0 for female and 1 for male. The handedness of the patient may be similarly represented using a binary value. The phenotype data may also be supplemented with an additional binary feature NoIQ with the value 1 if the patient is missing IQ scores and 0 otherwise. The phenotypic data may be received by a user manually entering the phenotypic data for the patient and storing the phenotypic data in a digital file on a memory or storage of a computer system. The phenotypic data may also be received by loading a previously stored digital file containing the phenotypic data for the patient. The values for the phenotypic features of the patient are appended to a feature list that is created by the patient.

The classification modules are trained offline prior to diagnosis of an unknown patient using training data from patients with known TBI diagnoses. The training data includes the structural MRI, rs-fMRI series, dMRI, and phenotype data for a group of patients, as well as a doctor's diagnosis of each patient. The anatomical, connectivity features, and/or network features extracted from the training data may be normalized to be zero mean and unit standard deviation across all patients in the training dataset. Any features with constant values across all patients in the training dataset may be excluded. The non-imaging phenotypic features are used without any normalization, and missing values of Verbal or Performance IQ are replaced by the respective population average.

A method for training a TBI diagnosis classifier in accordance with the present teachings will now be described. Initially, the training data is received. For each patient in a group of patients with known TBI diagnoses, previously stored structural MRI, rs-fMRI series, dMRI, connectivity data, network data, and phenotypic data may be loaded. The features are extracted from the training data. The anatomical, functional, and diffusion features may be extracted as described above. The connectivity and network features are extracted as further described herein. The resulting feature vector or set of values for each patient is saved to an electronic storage device. The collection of feature values for a given individual is designated as a training example, and the corresponding TBI diagnosis as its label.

A feature ranking method and number of features may be selected using cross-validation with multiple possible feature ranking methods. In some embodiments, for each cross-validation fold, rankings of features for the TBI-positive vs. TBI negative classifier are determined using a given feature ranking method, including but not limited to one of the following:

Analysis of Variance (ANOVA)

For each feature, the values of the feature for TBI-positive training examples and for TBI-negative trainings are placed into two samples. An ANOVA is performed on the two samples corresponding to positive feature scores and negative feature scores, respectively, and the resulting statistic value is used as the feature score for that feature.

Nested CV

For each feature, a Bayesian Gaussian TBI-positive vs. TBI-negative classifier is trained over the values of that feature and tested using nested cross-validation. The accuracy of the Bayesian Gaussian classifier for the feature, determined based on nested cross-validation testing, is used as the feature score for that feature.

Recursive Feature Elimination

Recursive feature elimination involves training the classifier (e.g., support vector machine (SVM), logistic regression classifier, naive Bayes classifier, k-nearest neighbor classifier, etc.) on all of the features using nested cross-validation, and scoring the features based on their effect on the classifier decision. The effect of each feature on the classifier decision is determined via the magnitude of feature weights for linear classifiers and through sensitivity analysis for nonlinear classifiers. The bottom 50% of the features are then eliminated from consideration and the procedure is repeated until there are 10 or fewer features. The feature score for each feature is a combination of the last round that that feature survived and the magnitude of the weight assigned to that feature by the classifier in the last round in which that feature survived. Accordingly, the last surviving features will have the highest feature scores.

For each feature ranking method, a classifier C is trained (for each cross-validation fold) to discriminate between TBI-positive and TBI-negative examples, using the top n features determined by the feature ranking method, with n ranging from 10, 20, 40, . . . , all of the features. The training process using a machine-learning algorithm to set parameters in order to maximize classification performance in the cross-validation fold training data. The machine-learning algorithm used to train the classifier varies based on the type of classifier (e.g., support vector machine (SVM), logistic regression classifier, naive Bayes classifier, k-nearest neighbor classifier, etc.). Each of these classifiers $C_{Mn}$, is then applied to predict a TBI diagnosis based on the same n features in the cross-validation fold test data, and an accuracy score is determined for each feature ranking method and number of features.

The accuracy scores for each feature ranking method and number of features are averaged over the cross-validation folds. For each feature ranking method, the highest accuracy score identifies the best number of features for that feature ranking method. If multiple numbers of features yield the same score, the largest number of features is used. The number of features and the combination of specific features may be different for each feature ranking method. In some embodiments, the best feature selection method is then selected as the feature selection whose highest accuracy score is higher than the highest accuracy scores of the other feature selection methods.

In some embodiments, a classifier is trained based on the entire set of training data using the selected feature ranking method and number of features. For example, the classifier is trained based on the entire set of training data to discriminate between TBI-positive and TBI-negative using the best number of features identified by the best feature ranking method. The specific features used for training, and the classifier's learned parameter values are stored in an electronic storage device, and these are accessed and used to calculate a diagnosis when the data from a new patient is received.

Methods in accordance with the present teaching may be implemented using any type of machine-learning classifier. In some embodiments, multiple types of classifiers may be trained, and their predictions combined to generate an overall diagnosis for a new patient. The classifier types may include but are not limited to, for example, a support vector machine (SVM), a logistic regression classifier, a naive Bayes classifier, and/or a k-nearest neighbors classifier. However, any type of classifier capable of handling numeric features may be used. The SVM may be implemented as a v-SVM with a variety of kernels. In some embodiments, a linear kernel SVM with a default setting of its regularization parameter may be used. The logistic regression classifier may be trained as a custom implementation with an L2 norm penalty on its weights. In some embodiments, the regularization parameter of the logistic regression may be set to 1. Three variations of the naive Bayes classifier may be used including a simple version, a version including kernel estimation of each feature, as compared with an assumption of normal distribution, and an updateable version trained incrementally. The k-nearest neighbors classifier uses a similarity measure between feature vectors to finding k most similar training examples to input data for a new patient, with values of k ranging from 1 to the square root of the number of data points. In some embodiments, correlation similarity is used as the similarity measure between feature vectors, and the square root of the number of data points is used as the number of neighbors. Methods as described above may be used to perform feature selection and training for each type of classifier. The training of the classifiers happens orthogonally to the feature ranking process, except for the recursive feature elimination method. The recursive feature elimination method uses the same classifier type as the current classifier being trained in its internal cross-validation.

Once the features are extracted for a new patient and stored in the patient's feature list, the values corresponding to the selected best features to be used by the trained classification module are read from the patient's feature list, and provided as input to the trained classification module. As described above, the classification module may include multiple types of trained classifiers. The classification module calculates predictions of the TBI diagnosis for each of the classifier types. That is, each trained classifier arithmetically combines the patient-specific feature values according to its parameters set during training to arrive at a respective prediction. The output of each classifier is weighted based on how well that type of classifier performed in isolation during cross-validation on the training set. For example, the weight of each classifier may be set to performance level (e.g., percentage of correct diagnosis) of that classifier type in isolation minus a baseline performance of predicting all training subjects to be TBI-negative.

A binary decision for the TBI diagnosis of the patient is determined by calculating a weighted average of the outputs of each of the classifiers and then rounding the resulting value. If the result after rounding is 0, then the diagnosis for the patient is TBI-negative. If the result after rounding is 1, then the diagnosis for the patient is TBI-positive. The predicted diagnosis for the patient may be output to a display device of a computer system and written to an electronic storage device.

At act 110 in the method 100 shown in FIG. 1, the prediction confidence is output. At act 112, feature influence is output. All of the types of classifiers described herein either produce a measure of confidence in the result directly, or are modifiable to do so. This measure may be standardized to lie in the [0,1] or other interval. A weighted average of these measures may be generated using the weights computed for generating the combined prediction. This confidence measure may be output together with the prediction for TBI diagnosis. This information may be used to determine how desirable it is to have a human scrutinize the determination, for instance, to allow doctor time to be focused on fewer patients overall.

Further, all of the types of classifiers support the calculation of a measure of feature influence. For example, the feature weights in a linear classifier may be used as the measure of feature influence. The feature influence measure is used to rank the features that had more influence on the classifier decision and output this information. For anatomical or other features, a brain image may be generated on which each feature weight is overlayed on the anatomical location of that feature. Both lists of ranked features and brain images showing the influence of the features may be output together with the prediction.

The following examples and representative procedures illustrate features in accordance with the present teachings, and are provided solely by way of illustration. They are not intended to limit the scope of the appended claims or their equivalents.

Data

Methods in accordance with the present teachings may rely on imaging data from an existing population (e.g., 20 or more) to train prediction models. Given the availability of a dataset containing both TBI patients and controls, non-imaging data may be available for each subject. For example, the non-imaging data may include but are not limited to phenotypic (e.g. age, IQ, etc.), genetic (e.g., does the subject have a variant of a gene predisposing the subject to Alzheimer's), and historical information (e.g. number, severity, and/or frequency of prior concussive episodes). The dataset may also contain imaging data for each subject. For example, the imaging data may include but are not limited to structural MRI data, resting state functional MRI data, diffusion MRI data (DTI/HARDI/DSI), and/or the like, and combinations thereof.

In some embodiments, the imaging data are acquired during both the subacute phase after the initial injury (e.g., "baseline data") and a certain period after the injury (e.g., "evaluation data" obtained, for example, six months later). In some embodiments, the dataset may be processed using tools in the FSL library of analysis tools for FMRI, MRI and DTI brain imaging data. The structural image from the first session may be used as the reference image for analysis, and grey and white matter masks generated with "fast." The structural image may be registered to the MNI template using "fnirt" and the transformation obtained may be inverted and applied to the AAL atlas, and masked with the grey matter mask to yield a subject-specific atlas with 116 regions of interest (ROIs). Any number of ROIs may be used.

Training a Classifier from Imaging Data

Figure 3A:
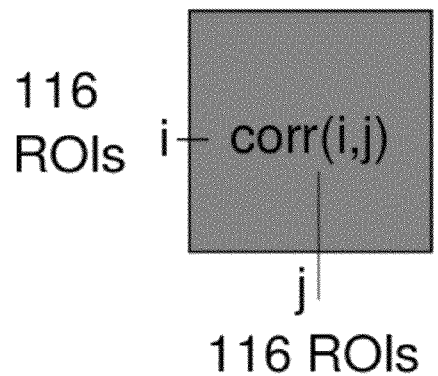
FIG. 3A shows a schematic illustration of an exemplary connectivity matrix having an entry (i, j) that contains a connectivity value between regions of interest (ROIs) i and j.
Figure 3B:
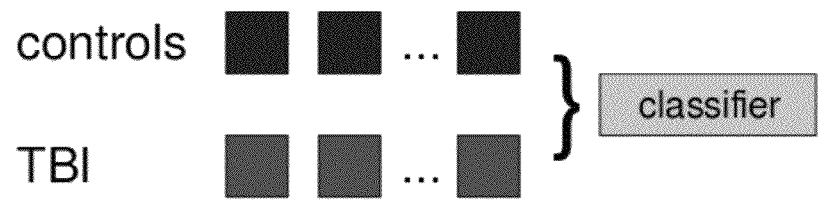
FIG. 3B shows a schematic illustration of an exemplary classifier distinguishing between TBI patients and controls based on connectivity matrices for patients in both groups.

As shown in FIG. 3B, and as described above, a classifier is a program that may learn to distinguish TBI patients from controls given connectivity matrices for subjects in both groups. In some embodiments, the matrices come from the existing dataset. The classifier may learn to distinguish TBI patient from controls in a multivariate manner. For example, all the entries in a structural connectivity matrix may be considered, as shown in FIG. 3A, and different variables may be weighed by how reliably the variables take different values between groups. The method will be described below in terms of an abstract connectivity matrix.

Using a Classifier to Produce Diagnostics of Damage

Figure 3C:
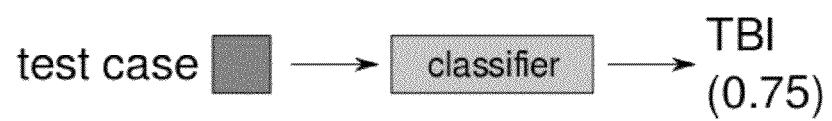
FIG. 3C shows a schematic illustration of an exemplary classifier outputting a prediction confidence.

Methods in accordance with the present teachings may rely upon applying a classifier to imaging data from a new subject—not a subject in the original dataset—in order to produce two different outputs, as described below. First, as illustrated in FIG. 3C, a synthetic biomarker quantifying damage may be provided as a single value representing the confidence with which the value predicts a subject belongs to the TBI group.

Figure 4A:
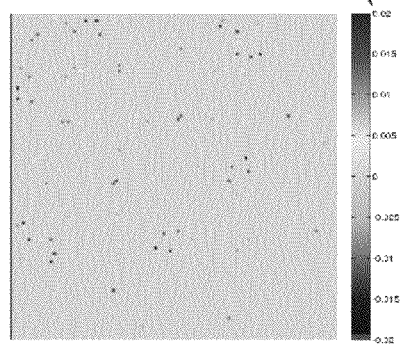
FIG. 4A shows a schematic illustration of an exemplary measure of feature influence corresponding to a representative pair of ROIs.
Figure 4B:
FIG. 4B shows a schematic illustration of a contribution map of all connections involving a representative ROI.

Second, a damage profile showing what aspects of the data led to the damage assessment may be provided. The damage profile may be provided as one value per pair of regions of interest, as shown, for example, in FIG. 4A. The influential connections may be a subset of the connections that the classifier is sensitive to, since the classifier was trained on a population with a variety of lesions. The population level perspective may be visualized by aggregating the contribution of all connections involving a particular ROI and coloring each voxel by the contribution of the ROI it belongs to, as shown in FIG. 4B.

The synthetic biomarker may be output by most classifiers, either directly (e.g., the probability of a class in a logistic regression model) or by converting a classifier-specific measure into a probability (e.g., for a support vector machine). The damage profile may be obtained by multiplying the value of each feature (e.g., matrix entry in the test subject data) by the influence of that feature in the classifier (e.g., the feature weight in a linear SVM) when making the correct class prediction. Intuitively, the damage profile provides a gauge of how much each feature was responsible for the prediction of the classifier.

The synthetic biomarker may be used both for diagnosis and for monitoring the degree of damage on a subject over time. Any classification model may be used as long as the model supports the output of a measure of confidence and some form of sensitivity analysis for each feature.

Using a Regression Model to Predict the Trajectory of Recovery

A classifier as described above may be applied to the imaging data collected for each subject at both baseline and evaluation points producing biomarker values and damage profiles at both stages. The dataset may then be used to create a regression model for predicting evaluation point damage profiles from the baseline damage profiles and other non-imaging subject data. The regression model may be used to predict the extent to which a new subject will have recovered by the point the evaluation period is over. The prediction may be made by taking into account not just the profile of damage in the subject, as gauged from imaging data, but also other relevant information about the subject that modifies how the imaging data should be taken into account.

Any regression model may be used in accordance with present teachings, including but not limited to a separate model for each of the entries in the damage profile (e.g., a linear regression or regression tree) or a model capable of predicting all of the entries simultaneously (e.g. a deep neural network).

Classification Experiments

Separate classification experiments may be carried out on each type of scalar measure considered. The procedure may be described in terms of an abstract connectivity matrix.

For each subject, the unique matrix entries may be converted into a 6670-dimensional vector. Thus, the dataset for experiments may correspond to a 50×6670 matrix of examples together with a label vector specifying whether a subject was a patient or a control. A linear SVM may be trained with default parameters in the young/old prediction task in a leave-one-subject-of-each-class-out cross-validation. Features in the training set of each fold may be selected and scored using a t-test. The number of features used may be determined by nested cross-validation inside the training set trying out 10, 25, 50, 100, 250, 500, 1000, 1500, 2000, 2500, 3000 or all features and selecting the number that leads to the best result (different from fold-to-fold).

Table 1 shows the sensitivity and specificity of the cross-validated classifier for the six different types of scalar measures considered for quantifying connectivity.

TABLE 1

Sensitivity and specificity for cross-validated classifier distinguishing mild TBI patients from controls

|  | FA | AD | MD | ADC | RD1 | RD2 |
|---|---|---|---|---|---|---|
| Specificity | 0.84 | 0.92 | 0.96 | 0.96 | 0.96 | 0.96 |
| Sensitivity | 0.88 | 0.92 | 0.88 | 0.96 | 0.88 | 0.83 |

The contribution of each feature—and hence each ROI-ROI connection—towards the classifier making the right prediction may also be estimated by multiplying the value of each feature across the test examples in each fold by the corresponding SVM weight for the correct class prediction (or 0, if the weight was not selected), and averaging across those examples. Given that each feature corresponds to a pair of ROIs, the contribution of a ROI may be obtained by aggregating the contributions of all the features for which it is in a pair.

The contribution map in FIG. 4B shows the contribution of each ROI by coloring each voxel with the value for the ROI to which it belongs. The contribution of the more important ROIs may be further decomposed into those of their more important connections. The decomposition is illustrated in Table 2 for ADC connectivity. Table 2 shows both the ROIs that contributed the most and the connections from those ROIs to other ROIs accounting for most of the contribution.

TABLE 2

The AAL ROIs that contributed the most towards successful classification (contribution as % of the total).

| ROI (total contribution) | To ROI | (contribution) |
|---|---|---|
| Temporal_Sup_L (0.065) | Frontal_Mid_L | 0.027 |
| | Frontal_Inf_Orb_L | 0.014 |
| | Temporal_Mid_L | 0.009 |
| | Angular_L | 0.007 |
| Frontal_Mid_R (0.061) | Cingulum_Ant_R | 0.014 |
| | Frontal_Mid_Orb_R | 0.012 |
| | Caudate_L | 0.006 |
| | Parietal_Inf_R | 0.006 |
| | SupraMarginal_R | 0.005 |
| | Postcentral_R | 0.004 |
| | Calcarine_R | 0.003 |
| Frontal_Inf_Orb_L (0.058) | Temporal_Inf_L | 0.021 |
| | Temporal_Sup_L | 0.014 |
| | Cerebelum_6_L | 0.006 |
| | Insula_L | 0.006 |
| Hippocampus_L (0.056) | Cerebelum_6_L | 0.017 |
| | Parietal_Inf_L | 0.013 |
| | Cingulum_Ant_L | 0.005 |
| | Putamen_L | 0.004 |
| | Cuneus_L | 0.004 |
| | Cerebelum_10_L | 0.004 |
| Frontal_Sup_L (0.054) | Rectus_L | 0.023 |
| | Cingulum_Ant_L | 0.018 |
| | Pallidum_R | 0.010 |
| ParaHippocampal_L (0.053) | Supp_Motor_Area_L | 0.012 |
| | Olfactory_L | 0.011 |
| | Occipital_Sup_L | 0.009 |
| | Cuneus_L | 0.005 |
| | Temporal_Pole_Sup_L | 0.005 |

The damage profile described earlier is related to the contribution of ROI-ROI connections. The ROIs highlighted for a subject will be a subset of the ROIs highlighted above, which include those with ROI-ROI connections that are informative for at least a subset of the population. Given enough subjects, the contribution map reflects all the different connectivity alteration types present). Depending on the training data and features used, other experimental results may be obtained.

The above-described methods for TBI diagnosis, feature extraction, and classifier training may be implemented on a computer using well-known computer processors, memory units, storage devices, computer software, and other components.

Figure 5:
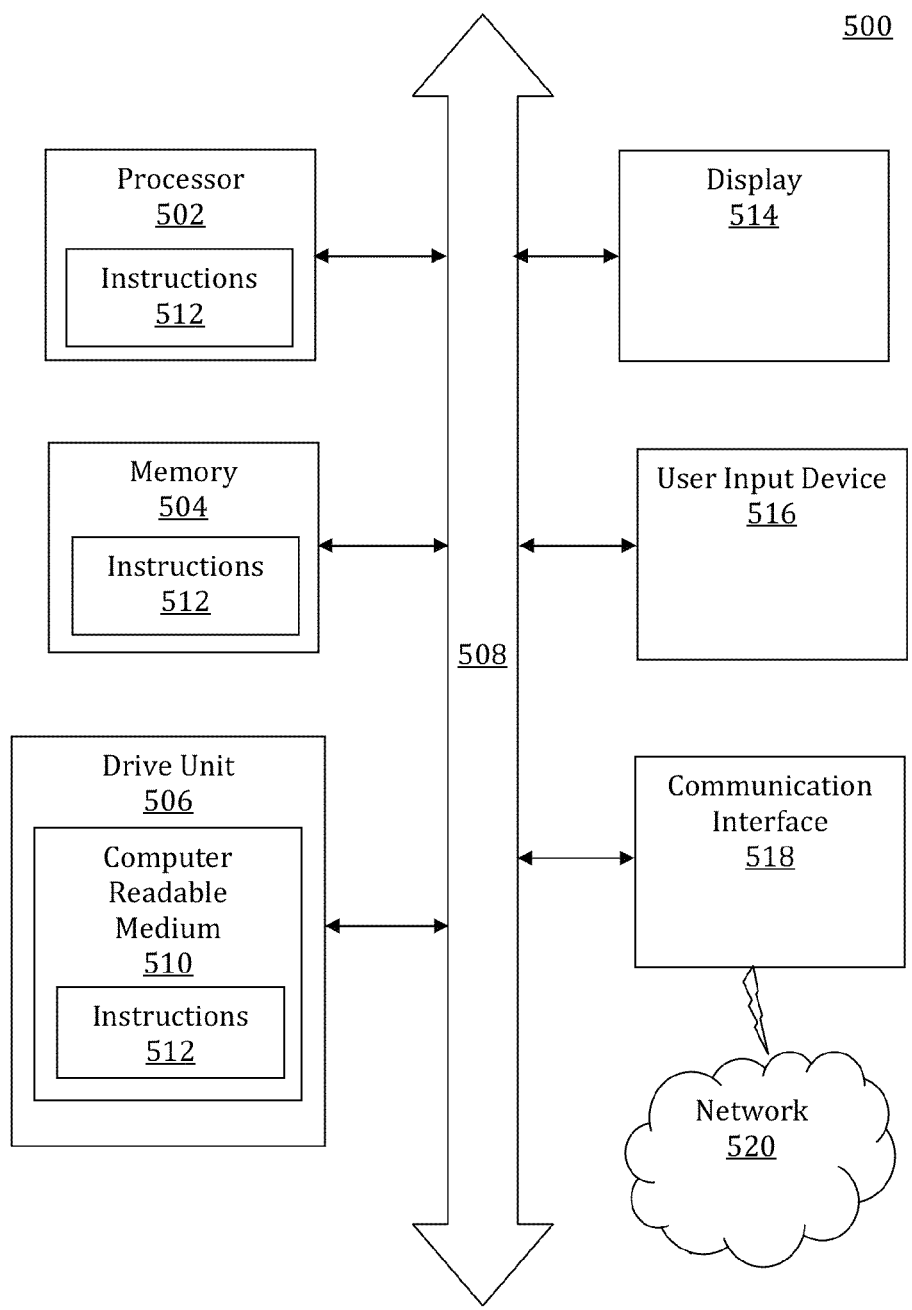
FIG. 5 shows a representative general computer system 500 for use with a system in accordance with the present teachings.

FIG. 5 depicts an illustrative embodiment of a general computer system 500. The computer system 500 can include a set of instructions that can be executed to cause the computer system 500 to perform any one or more of the methods or computer-based functions disclosed herein. The computer system 500 may operate as a standalone device or may be connected (e.g., using a network) to other computer systems or peripheral devices. Any of the components discussed above, such as the processor, may be a computer system 500 or a component in the computer system 500. The computer system 500 may implement a diagnostic system, of which the disclosed embodiments are a component thereof.

In a networked deployment, the computer system 500 may operate in the capacity of a server or as a client user computer in a client-server user network environment, or as a peer computer system in a peer-to-peer (or distributed) network environment. The computer system 500 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In some embodiments, the computer system 500 may be implemented using electronic devices that provide voice, video or data communication. Further, while a single computer system 500 is illustrated, the term "system" shall also be taken to include any collection of systems or sub-systems that individually or jointly execute a set, or multiple sets, of instructions to perform one or more computer functions.

As shown in FIG. 5, the computer system 500 may include a processor 502, for example a central processing unit (CPU), a graphics-processing unit (GPU), or both. The processor 502 may be a component in a variety of systems. For example, the processor 502 may be part of a standard personal computer or a workstation. The processor 502 may be one or more general processors, digital signal processors, application specific integrated circuits, field programmable gate arrays, servers, networks, digital circuits, analog circuits, combinations thereof, or other now known or later developed devices for analyzing and processing data. The processor 502 may implement a software program, such as code generated manually (i.e., programmed).

The computer system 500 may include a memory 504 that may communicate via a bus 508. The memory 504 may be a main memory, a static memory, or a dynamic memory. The memory 504 may include, but is not limited to, computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In some embodiments, the memory 504 includes a cache or random access memory for the processor 502. In alternative embodiments, the memory 504 is separate from the processor 502, such as a cache memory of a processor, the system memory, or other memory. The memory 504 may be an external storage device or database for storing data. Examples include a hard drive, compact disc (CD), digital video disc (DVD), memory card, memory stick, floppy disc, universal serial bus (USB) memory device, or any other device operative to store data. The memory 504 is operable to store instructions executable by the processor 502. The functions, acts or tasks illustrated in the figures or described herein may be performed by the programmed processor 502 executing the instructions 512 stored in the memory 504. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown in FIG. 5, the computer system 500 may further include a display unit 514, such as a liquid crystal display (LCD), an organic light emitting diode (OLED), a flat panel display, a solid state display, a cathode ray tube (CRT), a projector, a printer or other now known or later developed display device for outputting determined information. The display 514 may act as an interface for the user to see the functioning of the processor 502, or specifically as an interface with the software stored in the memory 504 or in the drive unit 506. A value or image based on the modeling may be output to the user on the display unit 514. For example, an image representing part of the patient with modulation or alphanumeric text representing a calculated value is indicated in the image.

Additionally, as shown in FIG. 5, the computer system 500 may include an input device 516 configured to allow a user to interact with any of the components of system 500. The input device 516 may be a number pad, a keyboard, or a cursor control device, such as a mouse, or a joystick, touch screen display, remote control or any other device operative to interact with the system 500.

In some embodiments, as shown in FIG. 5, the computer system 500 may also include a disk or optical drive unit 506. The disk drive unit 506 may include a computer-readable medium 510 in which one or more sets of instructions 512 (e.g., software) may be embedded. Further, the instructions 512 may embody one or more of the methods or logic as described herein. In some embodiments, the instructions 512 may reside completely, or at least partially, within the memory 504 and/or within the processor 502 during execution by the computer system 500. The memory 504 and the processor 502 also may include computer-readable media as described above.

The present teachings contemplate a computer-readable medium that includes instructions 512 or receives and executes instructions 512 responsive to a propagated signal, so that a device connected to a network 520 may communicate voice, video, audio, images or any other data over the network 520. Further, the instructions 512 may be transmitted or received over the network 520 via a communication interface 518. The communication interface 518 may be a part of the processor 502 or may be a separate component. The communication interface 518 may be created in software or may be a physical connection in hardware. The communication interface 518 is configured to connect with a network 520, external media, the display 514, or any other components in system 500, or combinations thereof. The connection with the network 520 may be a physical connection, such as a wired Ethernet connection or may be established wirelessly as discussed below. Likewise, the additional connections with other components of the system 500 may be physical connections or may be established wirelessly.

The network 520 may include wired networks, wireless networks, or combinations thereof. The wireless network may be a cellular telephone network, an 802.11, 802.16, 802.20, or WiMax network. Further, the network 520 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification may be implemented in digital electronic circuitry, or in computer software, firmware, or hardware, including the structures disclosed in this specification and their structural equivalents, or in combinations of one or more of them. Embodiments of subject matter described in this specification may be implemented as one or more computer program products, for example, one or more modules of computer program instructions encoded on a computer-readable medium for execution by, or to control the operation of, data processing apparatus. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer-readable medium may be a machine-readable storage device, a machine-readable storage substrate, a memory device, or a combination of one or more of them. The term "data processing apparatus" encompasses all apparatuses, devices, and machines for processing data, including but not limited to, by way of example, a programmable processor, a computer, or multiple processors or computers. The apparatus may include, in addition to hardware, code that creates an execution environment for the computer program in question (e.g., code that constitutes processor firmware, a protocol stack, a database management system, an operating system, or a combination thereof).

In some embodiments, the computer-readable medium may include a solid-state memory such as a memory card or other package that houses one or more non-volatile read-only memories. Further, the computer-readable medium may be a random access memory or other volatile re-writable memory. Additionally, the computer-readable medium may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the present teachings are considered to include any one or more of a computer-readable medium or a distribution medium and other equivalents and successor media, in which data or instructions may be stored.

In some embodiments, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

In some embodiments, the methods described herein may be implemented by software programs executable by a computer system. Further, in some embodiments, implementations may include distributed processing, component/object distributed processing, and parallel processing. Alternatively, virtual computer system processing may be constructed to implement one or more of the methods or functionality as described herein.

Although the present teachings describe components and functions that may be implemented in particular embodiments with reference to particular standards and protocols, the present invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described herein may be performed by one or more programmable processors executing one or more computer programs to perform functions by operating on input data and generating output. The processes and logic flows may also be performed by, and apparatus may also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The main elements of a computer are a processor for performing instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer may be embedded in another device, for example, a mobile telephone, a personal digital assistant (PDA), a mobile audio player, a Global Positioning System (GPS) receiver, to name just a few. Computer-readable media suitable for storing computer program instructions and data include all forms of non volatile memory, media and memory devices, including but not limited to, by way of example, semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, some embodiments of subject matter described herein may be implemented on a device having a display, for example a CRT (cathode ray tube) or LCD (liquid crystal display) monitor, for displaying information to the user and a keyboard and a pointing device, for example a mouse or a trackball, by which the user may provide input to the computer. Other kinds of devices may be used to provide for interaction with a user as well. By way of example, feedback provided to the user may be any form of sensory feedback (e.g., visual feedback, auditory feedback, or tactile feedback); and input from the user may be received in any form, including but not limited to acoustic, speech, or tactile input.

Embodiments of subject matter described herein may be implemented in a computing system that includes a back-end component, for example, as a data server, or that includes a middleware component, for example, an application server, or that includes a front end component, for example, a client computer having a graphical user interface or a Web browser through which a user may interact with an implementation of the subject matter described in this specification, or any combination of one or more such back end, middleware, or front end components. The components of the system may be interconnected by any form or medium of digital data communication, for example, a communication network. Examples of communication networks include but are not limited to a local area network (LAN) and a wide area network (WAN), for example, the Internet.

The computing system may include clients and servers. A client and server are generally remote from each other and typically interact through a communication network. The relationship of client and server arises by virtue of computer programs running on the respective computers and having a client-server relationship to each other.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 CFR §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A computer-implemented method for assessing a traumatic brain injury (TBI) in a patient, the method comprising:
   obtaining diffusion magnetic resonance imaging (dMRI) data from the patient;
   obtaining resting-state functional magnetic resonance imaging (rs-fMRI) data from the patient;
   extracting connectivity features between different regions of a brain of the patient, the connectivity features extracted from the rs-fMRI data obtained from the patient and/or from the diffusion magnetic resonance imaging (dMRI) data obtained from the patient;
   extracting network features from the connectivity features; and
   determining a TBI diagnosis for the patient based on at least the network features and the connectivity features using a trained classifier.

2. The computer-implemented method of claim 1, further comprising extracting anatomical features from structural MRI (sMRI), wherein the trained classifier uses the anatomical features.

3. The computer-implemented method of claim 1, further comprising extracting functional features from the rs-fMRI data, wherein the trained classifier uses the functional features.

4. The computer-implemented method of claim 1, wherein the determining is further based on phenotypic features of the patient, genetic features of the patient, medical history of the patient, or combinations thereof.

5. The computer-implemented method of claim 4, wherein the phenotypic features of the patient are selected from the group consisting of age of the patient, gender of the patient, handedness of the patient, verbal IQ of the patient, performance IQ of the patient, and combinations thereof.

6. The computer-implemented method of claim 1 wherein extracting the connectivity features comprises extracting the connectivity features for a first graph using the rs-fMRI data and for a second graph using the dMRI data.

7. The computer-implemented method of claim 4, wherein the medical history of the patient comprises information relating to previous concussive episodes experienced by the patient.

8. The computer-implemented method of claim 1, wherein the determining of the TBI diagnosis for the patient using the trained classifier comprises:
   determining the TBI diagnosis using a plurality of trained classifiers based on a subset of features selected from at least the network features and the connectivity features of the patient.

9. The computer-implemented method of claim 8, wherein the determining of the TBI diagnosis using the plurality of trained classifiers comprises:
   calculating a respective TBI diagnosis prediction from each of the plurality of trained classifiers;
   calculating a weighted average of the respective TBI diagnosis predictions, wherein each respective TBI prediction is weighted based on a performance level of the corresponding trained classifier in predicting TBI diagnoses of training examples; and
   determining the TBI diagnosis for the patient based on the weighted average of the respective TBI diagnosis predictions.

10. The computer-implemented method of claim 1, wherein the trained classifier is selected from the group consisting of a support vector machine classifier, a logistic regression classifier, a naive Bayes classifier, a k-nearest neighbor classifier, and combinations thereof.

11. The computer-implemented method of claim 1, further comprising:
   outputting a prediction confidence associated with the TBI diagnosis for the patient.

12. The computer-implemented method of claim 1, further comprising:
   outputting a measure of feature influence indicative of a relative influence of a feature on the TBI diagnosis for the patient.

13. The computer-implemented method of claim 12, wherein the outputting of the measure of the feature influence comprises:
   generating a list ranking the features based on feature weights used by the trained classifier.

14. The computer-implemented method of claim 1, further comprising:
   outputting a prediction of a recovery trajectory for the patient based on at least the network features and the connectivity features using the trained classifier.

15. The computer-implemented method of claim 14, wherein the outputting is further based on phenotypic features of the patient, genetic features of the patient, medical history of the patient, or combinations thereof.

16. The computer-implemented method of claim 1, further comprising:
   extracting anatomical features from sMRI data obtained from the patient during both a post-injury subacute phase and a subsequent evaluation phase;

extracting functional features from the rs-fMRI data obtained from the patient during both the post-injury subacute phase and the subsequent evaluation phase;

extracting connectivity features from the rs-fMRI data obtained from the patient during both the post-injury subacute phase and the subsequent evaluation phase; and predicting a recovery trajectory for the patient based on the anatomical features, the functional features, and the connectivity features using the trained classifier.

17. The computer-implemented method of claim 16, wherein the predicting is further based on phenotypic features of the patient, genetic features of the patient, medical history of the patient, or combinations thereof.

18. A system for assessing a traumatic brain injury (TBI) in a patient, the system comprising:

a computer processor;

a non-transitory memory coupled with the computer processor;

first logic stored in the non-transitory memory and executable by the computer processor to cause the computer processor to extract features from magnetic resonance imaging (MRI) data obtained from the patient;

second logic stored in the non-transitory memory and executable by the computer processor to cause the computer processor to determine a TBI diagnosis for the patient based on the features using a trained classifier;

third logic stored in the non-transitory memory and executable by the computer processor to cause the computer processor to output a confidence in the TBI diagnosis as a synthetic biomarker;

fourth logic stored in the non-transitory memory and executable by the computer processor to cause the computer processor to output a measure of feature influence indicative of a relative influence of a feature on the TBI diagnosis for the patient; and fifth logic stored in the non-transitory memory and executable by the computer processor to cause the computer processor to output a prediction of a recovery trajectory for the patient based on the features using the trained classifier.

19. The system of claim 18 further comprising:

sixth logic stored in the non-transitory memory and executable by the computer processor to cause the computer processor to extract a first connectivity of different regions of the patient using functional MRI;

seventh logic stored in the non-transitory memory and executable by the computer processor to cause the computer processor to extract a second connectivity of the different regions of the patient using diffusion MRI; and eighth logic stored in the non-transitory memory and executable by the computer processor to cause the computer processor to extract network features for the first connectivity and/or the second connectivity.

20. A system for assessing a traumatic brain injury (TBI) in a patient, the system comprising:

means for extracting anatomical features from structural magnetic resonance imaging (sMRI) data obtained from the patient;

means for extracting functional features from resting-state functional magnetic resonance imaging (rs-fMRI) data obtained from the patient;

means for extracting connectivity features from the rs-fMRI data obtained from the patient and/or from diffusion magnetic resonance imaging (dMRI) data obtained from the patient; and means for determining a TBI diagnosis for the patient based on at least the anatomical features, the functional features, and the connectivity features using a trained classifier.

21. A non-transitory computer-readable storage medium having stored therein data representing instructions executable by a programmed processor for assessing a traumatic brain injury (TBI) in a patient, the storage medium comprising instructions for:

extracting anatomical features from structural magnetic resonance imaging (sMRI) data obtained from the patient;

extracting functional features from resting-state functional magnetic resonance imaging (rs-fMRI) data obtained from the patient;

extracting connectivity features from the rs-fMRI data obtained from the patient and/or from diffusion magnetic resonance imaging (dMRI) data obtained from the patient; and determining a TBI diagnosis for the patient based on at least the anatomical features, the functional features, and the connectivity features using a trained classifier.

* * * * *